United States Patent [19]

Doshi et al.

[11] Patent Number: 5,766,552
[45] Date of Patent: *Jun. 16, 1998

[54] APPARATUS FOR RED BLOOD CELL SEPARATION

[75] Inventors: Sonal R. Doshi, Springfield, Pa.; John K. McGeehan, Woodbury; Wai Tak Law, Sewell, both of N.J.

[73] Assignee: ActiMed Laboratories, Inc., Burlington, N.J.

[*] Notice: The term of this patent shall not extend beyond the expiration date of Pat. No. 5,660,798.

[21] Appl. No.: 596,828

[22] Filed: Feb. 5, 1996

Related U.S. Application Data

[63] Continuation-in-part of Ser. No. 49,862, Apr. 20, 1993, Pat. No. 5,652,148, and a continuation-in-part of Ser. No. 203,778, Mar. 1, 1994, abandoned, which is a continuation-in-part of Ser. No. 49,862, Apr. 20, 1993, Pat. No. 5,652,148.

[51] Int. Cl.⁶ .................. G01N 1/28; B01L 11/00
[52] U.S. Cl. .................. 422/101; 422/56; 422/77; 436/526; 436/527; 436/531; 436/535; 436/827
[58] Field of Search .................. 435/7.25; 436/827, 436/526, 527, 531, 63, 177, 178; 422/61, 56–60, 101

[56] References Cited

U.S. PATENT DOCUMENTS

| | | |
|---|---|---|
| 2,330,410 | 9/1943 | Cyr. |
| 3,092,465 | 6/1963 | Adams et al. |
| 3,462,361 | 8/1969 | Greenwalt et al. |
| 3,630,957 | 12/1971 | Rey et al. |
| 3,663,374 | 5/1972 | Moyer et al. |
| 3,723,064 | 3/1973 | Liotta. |
| 3,917,453 | 11/1975 | Milligan et al. |
| 4,005,187 | 1/1977 | Kilthau et al. |
| 4,053,420 | 10/1977 | Marx. |
| 4,155,854 | 5/1979 | Marx. |
| 4,238,334 | 12/1980 | Halbfoster. |
| 4,246,107 | 1/1981 | Takenaka et al. |
| 4,246,693 | 1/1981 | Onuki et al. |
| 4,250,257 | 2/1981 | Lee et al. |
| 4,252,653 | 2/1981 | Beck et al. |
| 4,256,693 | 3/1981 | Kondo et al. |
| 4,258,001 | 3/1981 | Pierce et al. |
| 4,288,228 | 9/1981 | Oberhardt. |
| 4,310,399 | 1/1982 | Columbus. |
| 4,330,299 | 5/1982 | Cerami. |
| 4,366,244 | 12/1982 | Pascal ......... 435/11 |
| 4,371,515 | 2/1983 | Chu. |

(List continued on next page.)

FOREIGN PATENT DOCUMENTS

| | | |
|---|---|---|
| 0353587 | 2/1990 | European Pat. Off. |
| 2239197 | 6/1991 | United Kingdom. |

OTHER PUBLICATIONS

Bunce et al. *Disposable Analytical Devices Permitting Automatic, Timed, Sequential Delivery of Multiple Reagents*, Analytical Chemical Acta. vol. 249, pp. 263–269, 1991.

Bernstein. *Lowering Blood Cholesterol to Prevent Heart Disease*, Journal of the American Medical Association, vol. 253, No. 14, pp. 2080–2086, Apr. 12, 1985.

*Primary Examiner*—Jan Ludlow
*Attorney, Agent, or Firm*—Iver P. Cooper

[57] ABSTRACT

Red blood cells are removed from whole blood or a fraction thereof by agglutinating whole blood with a mixture of a free agglutinating agent and nucleating particles having agglutinating agent intimately associated therewith to form clusters of red blood cells. High molecular weight polyethylene glycol may be added further to enhance agglutination. The clusters of red blood cells are much larger than the size of individual red blood cells, so that the clusters can easily be filtered through a porous medium. The plasma, which is substantially free of red blood cells, is further passed through a filter that optionally contains an additional agglutinating agent. Flow-delay additives may be provided to retain the fluid sample in contact with a reagent for a predetermined time.

16 Claims, 2 Drawing Sheets

U.S. PATENT DOCUMENTS

| | | |
|---|---|---|
| 4,416,777 | 11/1983 | Kuroda et al. . |
| 4,450,104 | 5/1984 | Jordan . |
| 4,477,575 | 10/1984 | Vogel et al. . |
| 4,493,793 | 1/1985 | Chu . |
| 4,522,786 | 6/1985 | Ebersole . |
| 4,522,923 | 6/1985 | Deutsch et al. . |
| 4,526,871 | 7/1985 | Avrameas et al. . |
| 4,532,107 | 7/1985 | Siddiqi . |
| 4,532,232 | 7/1985 | Larsson et al. . |
| 4,549,952 | 10/1985 | Columbus . |
| 4,554,257 | 11/1985 | Aladjem et al. ........................ 436/519 |
| 4,587,099 | 5/1986 | Rothe et al. . |
| 4,587,102 | 5/1986 | Nagatomo et al. . |
| 4,594,327 | 6/1986 | Zuk et al. . |
| 4,605,629 | 8/1986 | Lange et al. . |
| 4,615,983 | 10/1986 | Koyama . |
| 4,618,476 | 10/1986 | Columbus . |
| 4,678,757 | 7/1987 | Rapkin et al. . |
| 4,680,274 | 7/1987 | Sakai et al. . |
| 4,693,985 | 9/1987 | Degen et al. . |
| 4,738,823 | 4/1988 | Engelmann . |
| 4,753,776 | 6/1988 | Hillman et al. . |
| 4,765,895 | 8/1988 | Schlueter et al. . |
| 4,786,603 | 11/1988 | Wielinger et al. . |
| 4,803,153 | 2/1989 | Shibata et al. . |
| 4,810,394 | 3/1989 | Masuda . |
| 4,816,224 | 3/1989 | Vogel et al. . |
| 4,839,296 | 6/1989 | Kennedy et al. . |
| 4,855,108 | 8/1989 | Masuda et al. . |
| 4,861,712 | 8/1989 | Bartl et al. . |
| 4,870,005 | 9/1989 | Akiyoshi et al. . |
| 4,876,067 | 10/1989 | Deneke et al. . |
| 4,879,340 | 11/1989 | Moriguchi et al. . |
| 4,883,764 | 11/1989 | Kloepfer . |
| 4,906,439 | 3/1990 | Grenner . |
| 4,910,150 | 3/1990 | Doeding et al. . |
| 4,917,799 | 4/1990 | Masuda et al. . |
| 4,923,680 | 5/1990 | Nelson . |
| 4,933,092 | 6/1990 | Aunet et al. . |
| 4,933,297 | 6/1990 | Lu . |
| 4,940,668 | 7/1990 | Wardlaw et al. . |
| 4,946,603 | 8/1990 | Laugharn et al. . |
| 4,959,305 | 9/1990 | Woodrum . |
| 4,959,324 | 9/1990 | Ramel et al. . |
| 4,963,498 | 10/1990 | Hillman et al. . |
| 4,966,784 | 10/1990 | Tanaka et al. . |
| 4,987,085 | 1/1991 | Allen et al. . |
| 4,990,457 | 2/1991 | Tanaka et al. . |
| 5,051,237 | 9/1991 | Grenner et al. . |
| 5,055,195 | 10/1991 | Trasch et al. . |
| 5,064,541 | 11/1991 | Jeng et al. . |
| 5,104,812 | 4/1992 | Kurn et al. . |
| 5,110,550 | 5/1992 | Schlipfenbacher et al. . |
| 5,118,428 | 6/1992 | Sand et al. . |
| 5,135,719 | 8/1992 | Hillman et al. . |
| 5,169,789 | 12/1992 | Berstein ........................ 436/501 |
| 5,185,127 | 2/1993 | Vonk . |
| 5,213,965 | 5/1993 | Jones . |
| 5,217,905 | 6/1993 | Marchand et al. . |

APPARATUS FOR RED BLOOD CELL SEPARATION

BACKGROUND OF THE INVENTION

1. Field of the Invention

The present invention relates to a method and apparatus for separating red blood cells from whole blood.

The present application is a continuation-in-part of application Ser. No. 08/049862, filed Apr. 20, 1993, now U.S. Pat. No. 5,652,148, and a continuation in part of application Ser. No. 08/203,778, filed Mar. 1, 1994, now abandoned which is a continuation in part of application Ser. No. 08/049,862, filed Apr. 20, 1993, now U.S. Pat. No. 5,652,148, the entire contents of both of which are hereby incorporated by reference.

2. Description of the Background Art

The ability to measure a wide variety of physiologically active compounds, both naturally occurring and synthetic, has become of increasing importance as an adjunct to both diagnosis and therapy. While for the most part such assays have required clinical laboratory determinations, there is an increasing awareness of he importance of being able to conduct assays in a physician's office or in the home. These environments require that the assay have a simple protocol and be relatively free of sensitivity to small changes in the conditions under which the assay is carried out. Importantly, inaccurate measurements of reagents and sample should, whenever feasible, be avoided. A number of systems have been developed to address the various problems associated with analysis outside of the clinical laboratory.

One analyte of importance is cholesterol. There is a clearly established relationship between total blood cholesterol (mainly the LDL fraction) and coronary artery disease (*J. A. M. A.* 253: 2080–2086, 1985). New guidelines have been established for adults to identify risk groups associated with blood cholesterol levels. Since cholesterol levels can be controlled by both diet and cholesterol lowering drugs, for those individuals at risk, the ability to monitor one's own cholesterol at home is useful in reducing the potential for heart disease. The measurement of other naturally occurring compounds of physiological importance, such as glucose, lipoproteins, etc., as well as synthetic drugs, is also of great interest, as assays become more sensitive and patients can more diligently exercise control.

In clinical assays, the separation of serum or plasma from whole blood is extremely important, since it is often difficult to conduct the analysis of dissolved blood components without interference from the red blood cells. Serum or plasma is conventionally separated from erythrocytes by centrifuging. Centrifugation, however, causes other problems, because one must then separate the supernatant from the blood cake. Moreover, this method is not available for use in home or office diagnostic assays.

Using whole blood with diagnostic devices in home or office assays gives rise to further problems. In these devices, it is customary to use reagents which cause a color change if the analyte is present (or, alternatively, if it is absent). Turbid or colored solutions, such as whole blood, may interfere with the readings.

Means for fractionating whole blood into blood cell plasma fractions are known in the art.

Vogel et al., in U.S. Pat. No. 4,447,575 disclose a process for separating plasma or serum from whole blood using a filter made of glass fibers. The glass fibers used have an average diameter of 0.2 to 5 microns, and a density of about 0.1 to 0.5 g/cm. Whole blood is placed onto a layer of glass fibers, and plasma is generated by retardation of flow of the cells. Plasma is collected at the other side of the glass fibers.

Another approach to separating red blood cells from whole blood is shown in Hillman et al., U.S. Pat. No. 4,753,776. In this patent, capillary action is used to pull whole blood through a glass microfiber filter by retarding the flow of the cells.

Allen et al., in U.S. Pat. No. 4,987,085, disclose a device and method for separating plasma from whole blood via filtering system with descending pore size to provide for successive removal of red blood cells without lysis. A combination of glass fiber membranes and cellulosic membranes is used to minimize red blood cell lysis while removing red blood cells.

Kondo et al., in U.S. Pat. No. 4,256,693, disclose a multilayered integral chemical analysis element for blood comprising a filter layer capable of removing formed components from the blood. The filter layer may be made of at least one component selected from paper, unwoven fabric, sheet-like filter material composed of powders or fibers such as man-made fibers or glass fibers, and membrane filters having suitable pore sizes. The filter layer separates the formed components of the blood at one time, or successively, such as in the order of leukocytes, erythrocytes, and platelets.

Other filtration systems are described in U.S. Pat. Nos. 3,092,465; 3,630,957; 3,663,374; 4,246,693; 4,246,107; and 2,330,410. Some of these filters employ membranes with small pores. A disadvantage of these filters is that blood can only penetrate through the membrane filter very slowly and in small amounts, because the membrane is very easily blocked. This results in a reaction which takes longer than it desirable.

Unfortunately, blood separation devices using glass fiber filters or membrane tend to retain significant amounts of serum or plasma, and display a relatively slow speed of separation. This presents a problem with diagnostic devices which are quantitative, as there must be sufficient sample present in the detection area to provide a reliable indication of the quantity of analyte detected. If insufficient sample flows through the filter, a false low reading will be obtained. Moreover, devices intended for home or office use should be convenient to use and should provide an indication of the analyte within a reasonably short period of time. It is thus essential to remove unwanted red blood cells to allow most of the remainder of the blood to pass through the separation device, and then filter the blood relatively quickly.

To solve these problems, test papers have been coated with semi-permeable membranes (U.S. Pat. No. 3,092,465), and swellable films into which only the dissolved components of the blood can penetrate, leaving the erythrocytes (U.S. Pat. No. 3,630,957). These two methods are only useful for testing low molecular weight components of blood such as glucose or urea. Higher molecular weight components of the blood such as lipids, or substrates bound to serum protein, such as bilirubin, cannot be determined in this way because they are not able to penetrate into the film or to pass through the semipermeable membrane.

Alternative solutions include covering diagnostic agents with membrane filters for separating the blood cells, as disclose in U.S. Pat. Nos. 3,663,374 and 4,246,693. A disadvantage with these diagnostic agents is that the blood can only penetrate through the membrane filter very slowly and in small amounts, because the membrane is very easily blocked. This results in a reaction which takes longer than is desirable.

U.S. Pat. Nos. 4,246,107 and 2,330,410, teach that lymphocytes and leukocytes can be separated from blood when the blood is filtered through a layer of synthetic resin fibers with an average fiber diameter of from 5 to 20 microns for lymphocytes, and from 3 to 10 microns for leukocytes. However, since the erythrocytes preponderantly pass through the filter with the plasma, these filters are not suitable for obtaining plasma.

Red blood cells can also be removed from whole blood samples by contacting a whole blood sample with an agglutinating agent. One type of red blood cell agglutinating agent is a lectin, a family of sugar binding protein first identified in plants. Red blood cells can be removed from whole blood by contacting the whole blood with a lectin, which attaches itself to specific glycoproteins on the red blood cell membrane and forms large masses by agglutination of the cells. However, when lectins contact red blood cells, cross-linking occurs to form a gel. The presence of this gel in a filter greatly reduces the flow of blood through a filter, and therefore limits the amount of plasma recovered.

Sand et al., in U.S. Pat. No. 5,118,428, disclose using an acid, such as citric, acetic or ascorbic acid, to agglutinate the red blood cells for separation from whole blood. However, use of an acid lowers the pH of the plasma, which may interfere with subsequent analyses.

Trasch et al., in U.S. Pat. No. 5,055,195, disclose the use of erythrocyte-retention substrates which contain two strongly polar groups which are connected by a non-polar bridge which serves as a spacer. These substrates change the polarity of the surface of the erythrocytes and cause them to agglutinate. The agglomerates formed in the blood can then be readily separated by filtration.

Zuk, in U.S. Pat. No. 4,594,327, teaches a method for separating red blood cells from whole blood by combining the whole blood sample with a red blood cell binding agent. This mixture is then filtered through a solid bibulous agent.

Rapkin et al., U.S. Pat. No. 4,678,757, disclose a method for separating blood into fluid and cellular fractions for diagnostic tests. The whole blood is introduced into a carrier containing a layer of carbohydrate, which separates the fluid from the cellular fractions.

Hillman et al., in U.S. Pat. Nos. 4,753,776 and 5,135,719, disclose a method for separating plasma from red blood cells wherein a low pressure filter is interposed in a pathway between an inlet port and a reaction area. Capillary force is the sole driving force for the movement of plasma from the filter to the reaction area. The filter is made of glass microfiber filters which can operate in the presence or absence of agglutins.

A device for separating plasma or serum from whole blood is disclosed in Aunet et al., U.S. Pat. No. 4,933,692. This device consists of a matrix of hydrophilic sintered porous material with at least one red blood cell agglutinating agent incorporated therein. An optional filter containing the same agglutinating agent is added to give a filter combination that yields plasma which is about 97% free of red blood cells.

Laugharn et al., in U.S. Pat. No. 4,946,603, describe a filter means to retain blood cells which pass through a matrix of hydrophilic sintered porous material to which at least one red blood cell agglutinating agent has been applied. The agglutinating agents used include natural and synthetic water soluble polymers, including hexadimethriine bromide, polylysine, and anti-red blood cell antibodies. The agglutination process is enhanced by incorporating substances such as polyvinyl pyrrolidone, which function as dielectrics, allowing charged cells to approach one another and by crosslinking by antibody and/or other agglutinins.

Bernstein, in U.S. Pat. No. 5,169,789, discloses a device for solid phase immunodiffusion assay in which inhibitors, red blood cells and the like can be removed by adding adsorbent materials, such as beads, kaolin, antibody or antigen coated particles or lectin coated particles, before the ligand receptor assay can be performed. There is no disclosure of how these adsorbent materials are prepared.

Many of the most commonly used assays in disposable assay devices require an incubation step, such are requiring enzymes to act on the sample, such as determinations of cholesterol, glucose, uric acid, and the like. Additionally, enzymes are often used as labels in immunoassay. In a conventional enzyme immunoassay, an enzyme is covalently conjugated with one component of a specifically binding antigen- antibody pair, and the resulting enzyme conjugate is reacted with a substrate to produce a signal which is detected and measured. The signal generated by the enzyme, in either the conventional or the immunoassay, may be a color change, detected with the naked eye or by a spectrophotometric technique.

However, despite many attempts by prior workers to provide means to separate red blood cells from whole blood quickly an and efficiently, there are still many disadvantages to the methods described above.

Ideally, a disposable assay device should include a means to delay the flow of the sample through the device for a predetermined time to permit incubation of the sample with the reagents or indicators present in a particular region of the device. After the incubation period, which is generally on the order of a few minutes or less, the sample then flows to the next region of the device for further processing.

An ideal flow delay means should work like a valve, with a "closed" and an "open" state. When the flow delay means is in the "closed" state, fluid flow should stop. When the device is in the "open" sate, fluid should flow through the flow-delay valve with little or no restriction, and the flow rate of the fluid through the device should be substantially unchanged.

A wide range of disposable analytical devices have been developed which include means to control flow of fluids therethrough. However, none of these previously developed devices has a valve-like means to control the flow of fluids.

Although there has been no previous disclose of assay devices having a valve-like means to control fluid flow, a number of disposable analytical devices include means for delaying flow. Examples of these can be found in Deutsch et al., U.S. Pat. No. 4,522,923; Ebersone, U.S. Pat. No. 4,522, 786; Jones, U.S. Pat. No. 5,213,965; Vonk, U.S. Pat. No. 5,185,127.

Assay devices in which contact between layers is delayed by physically separating the layers until the operator places the layers into contact with each other are shown in Deneke et al., U.S. Pat. No. 4,876,076; and Ramel et al., U.S. Pat. No. 4,959,324.

Other means for controlling flow of sample through assay devices include those of Woodrum, U.S. Pat. No. 4,959,305, reversibly immobilized assay reagents; Columbus, U.S. Pat. No. 4,549,952, viscosity increasing means; Bruce et al., *Analytical Chemica Acta* 249:263–269, 1991, expansion of compressed foam; Hillman et al., U.S. Pat. No. 4,963,498, agglutination of binding pairs; Kurn et al., U.S. Pat. No. 5,104,812, interrupting capillary flow.

Physical barrier to interrupt flow are shown in Columbus, U.S. Pat. Nos. 4,310,399 and 4,618,476 and Grenner et al., U.S. Pat. No. 5,051,237.

Liquid flow through a filter is controlled by reactions between the sample and a component of the filter, such as in Marchand et al., U.S. Pat. No. 5,127,905 and Tanaka et al., U.S. Pat. No. 4,966,784.

Impregnated layers which are non valve-like in their actions are shown in Liotta, U.S. Pat. No. 3,723,064; Engelmann, U.S. Pat. No. 4,738,823; Nagatomo et al., U.S. Pat. No. 4,587,102; Koyama et al., U.S. Pat. No. 54,615,983; Rothe et al., U.S. Pat. No. 4,587,099; and Nelson, U.S. Pat. No. 4,923,680.

Moreover, none of the above-noted patents provides a reliable means for metering the rate of flow delay through a layer in order to retain a sample in contact with a reagent for a predetermined length of time.

No admission is made that any of the patents or other background art cited above constitutes prior art.

SUMMARY OF THE INVENTION

The present invention provides an efficient and rapid means for removing red blood cells from a blood sample. This method can be used in conjunction with an assay device for use in a physician's office or the home, as the red blood cells are rapidly removed from whole blood while most of the serum or plasma passes rapidly through the device for subsequent analysis.

The device of the present invention provides cluster forming means made of a porous material such as an absorbent pad which contains therein both agglutinating agents and nucleating particles. Although the agglutinating agent may be coated onto or bound to the particles, there is preferably some free, i.e., unbound and uncoated, agglutinating agent present in the porous material in order to form clusters of red blood cells quickly and efficiently. The combination of free agglutinating agent and nucleating particles containing agglutinating agent provides for rapid and substantially complete agglutination of red blood cells, allowing high flow rates through this part of the assay device while still achieving a substantially complete removal of red blood cells.

For the purpose of the present invention, "substantially complete removal" of red blood cells means that the red blood cells are removed from the sample such that there is essentially no interference with any subsequent assay performed on the sample.

Conventionally coated particles are prepared by mixing the particles with the agglutinating material to be used, maintaining the particles in contact with the agglutinating material for sufficient time to adsorb, absorb, conjugate, or otherwise coat the agglutinating agent to the surface of the particles, and then washing the particles to remove excess agglutinating agent. Conventionally prepared coated particles are thus substantially free of agglutinating agent that is not intimately associated with the particles.

For the purpose of the present invention, when the agglutinating agent is described as being "intimately associated with" the particles, it means that the agglutinating agent is coated onto the particles, adsorbed or absorbed onto the particles, conjugated or covalently bound to the particles, or otherwise associated with the particles so that the agglutinating agent and the particles are not substantially separated from each other by normal rinsing or washing of the particles with water.

In the present invention, on the other hand, there is preferably free, i.e., unbound or uncoated, agglutinating agent mixed with the particles. Desirably at least about 25% of the total agglutinating agent is mixed with, but is not intimately associated with, the particles. The agglutinating agent can be conjugated to the nucleating particles, or can be coated, adsorbed, or absorbed onto the nucleating particles. It is essential, however, that there be some free, i.e., unbound or uncoated, agglutinating agent present in the system along with the particles in order to provide optimum formation of red blood cell clusters. By contacting a fluid sample containing red blood cells with a mixture of free agglutinating agent and particles intimately associated with agglutinating agent, red blood cells are agglutinated and trapped by the pad, while the remainder of the fluid sample flows through readily. It is believed that the agglutinating agent binds red blood cells, forming agglutinates thereof, while the nucleating particles provide a nucleus for formation of clusters of the agglutinates. However, it should be understood that the practice of this invention is not dependent upon the correctness of this theory.

In one embodiment of the present invention, high molecular weight polyethylene glycol (MW>10,000) is added to the combination of agglutinating agent and nucleating particles. The polyethylene glycol enhances the formation of clusters.

The blood separation means of the present invention has the following advantages:

(1) Since whole blood can be directly used as a sample for assay, the processing operation is very simple and convenient. There is no retirement to separate the red blood cells from the sample prior to conducting the assay. Furthermore, the preparation time up to the chemical analysis per se is very short. Despite this, the red blood cell separating means of this invention can permit dry-chemical analysis of blood with accuracy equivalent to wet-method chemical analysis of components dissolved in blood using serum or plasma as a sample.

(2) The sample fluid resulting from the filtration of formed components from whole blood transferred to the porous material is supplied smoothly to the analysis area of an assay device. Because the whole blood travels through the absorbent pad and secondary filter rather rapidly and most of the liquid traverses the red blood cell removing means, an accurate determination can be made of the analyte of interest.

In a preferred embodiment, a flow delay means is provided in the device to delay the flow of the fluid sample after the red blood cells have been removed. This permits incubation of the fluid sample for prolonged contact with an enzyme or chemical reagent where necessary. The flow delay device inhibits sample flow for a predetermined discrete period of time, after which the sample completely flows through the flow delay means for further processing.

DETAILED DESCRIPTION OF THE PREFERRED EMBODIMENTS

Figure 1:
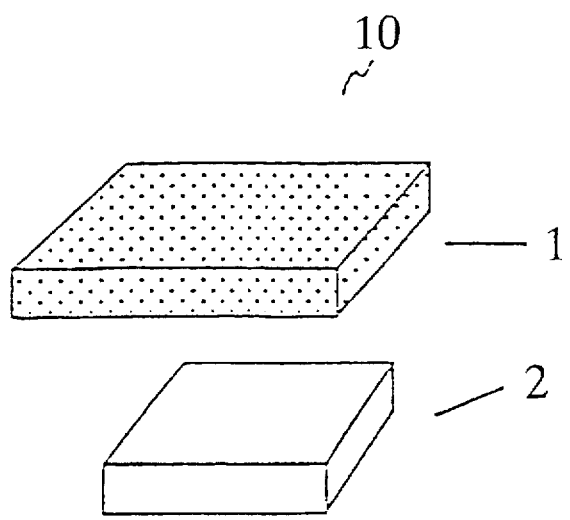
FIG. 1 shows a device according to the invention.

Blood is composed of two parts: (a) plasma, the fluid portion; and (b) formed elements, the blood cells and platelets suspended in the fluid. The plasma accounts for about 55% of the total volume of blood, and is about 92% water, 7% protein and less than 1% other substances. The principal plasma proteins are the globulins, albumin and fibrinogen. Plasma from which fibrinogen has been removed is called serum. The suspended particles include erythrocytes (red blood cells), leukocytes (white blood cells) and thrombocytes (platelets). Most of the blood cells (corpuscles) are red blood cells. White blood cells are larger than red blood cells, but fewer in numbers.

For purposes of the instant invention, the term "whole blood" indicates plasma which still contains a substantial number of red blood cells, even if some red blood cells had previously been removed. The removal of red blood cells from a whole blood sample is a form of blood fractionation. Blood fractionation is important in clinical chemistry because chromogenic analysis is generally used to determine the concentration of particular components dissolved in blood. The presence of a particular component is signaled by color production or color change. The presence of red blood cells in whole blood interferes with the reaction of the chromogenic analysis because of the turbidity and color of the whole blood. therefore, it is important to remove red blood cells from whole blood prior to using the remaining serum or plasma in the analysis of dissolved blood components.

Thus, it is desirable to provide means for removing substantially all of the red blood cells from a sample of whole blood. For purposes of this invention, a sample is considered to be substantially free of red blood cells when any red blood cells that may remain in the sample do not interfere with the accuracy of the analysis for the analyte sought to be detected in the sample. That is, any red blood cells that may remain in the sample are not detectable or do not interfere with the analytic method employed for detection of the analyte of interest.

Agglutinating Agents

Although many agglutinants for red blood cells are known, the agglutinants used in the present invention must be such that they do not interfere with any subsequent analysis. Preferably, the agglutinating agents have fast action and a short reactivation time from the dry to the wet state, and are non- specific to blood types as well as being stable and inexpensive. Agglutinating agents can readily be selected by screening tests with whole blood samples, which is well within the skill of the art.

The preferred agglutinants are lectins, including concanavalin A, wheat germ agglutinin, and the agglutinins of Glycin max. and Phaseolous vulgaris, either separately or in combination. Lectins are proteins, widely distributed in nature, which are able to agglutinate erythrocytes and many other types of cells. More specifically, the term "lectin" denotes "a sugar- bonding protein or glycoprotein of non-immune origin which agglutinates cells and.or precipitates glycoconjugates," Goldstein et al., Nature 285: 66(1980). Lectins occur primarily in plant seeds, but they also occur in roots, leaves and bark. In addition, lectins are present in invertebrates such as clams, snails, and horseshoe crab, and in several vertebrate species.

Members of the lectin family include concanavalin A, arbin, ricin, as well as soybean agglutinin and wheat germ agglutinin. Further background on lectins can be found in H. P. Schnebli and J. Bachi, "Reactions of Lectins with Human Erythrocytes," Exot. Cell. Research 91 (1975) and "Lectins and Lectin Conjugates" , a general lectin catalogue produced by EY Laboratories, Inc., San Mateo, Calif..

Alternatively, antibodies can be used as agglutinating agents. The antibodies used have a binding affinity for a determinant present on the surface of red blood cells. Antibodies reactive with any antigen present on the surface of a red blood cell can be used, including but not limited to major histocompatibility antigens, cell surface proteins, cell surface carbohydrates, and cell surface glycoproteins. Antibodies for agglutinating erythrocytes are well known, and may be based upon antibodies which recognize various antigenic surface constituents or the erythrocytes, including proteins, glycoproteins, glycolipids, and lipoproteins. Antibodies which recognize these constituents may be prepared by conventional techniques using the membrane, or the purified constituents themselves, as immunogens. These antibodies may be monoclonal or polyclonal in nature. Either the intact antibody, or specific binding fragments thereof, may be used as agents to agglutinate the erythrocytes.

It has also been discovered that polyethylene glycol can be added to the combination of the agglutinating agent and nucleating particles to enhance formation of clusters from red blood cells. As shown in Table 1 above, the agglutination rate is enhanced by the addition of polyethylene glycol having a molecular weight of above about 10,000. It was found that polyethylene glycol having a molecular weight of about 35,000 was particularly suitable, but that polyethylene glycol having molecular weights of about 20,000 can also be used. The polyethylene glycol can be incorporated in the pad in the same manner as the agglutinating agent and nucleating particles, preferably by impregnation from a solution thereof.

Further discussion of erythrocyte agglutinating and binding material is given in Hillyard et al., U.S. Pat. No. 5,086,002, which patent is hereby incorporated by reference in its entirety.

It is desirable that the agglutinating agent be capable of agglutinating all red blood cells of the species, e.g., human, to which the subject belongs. If a single monoclonal antibody is not available which is not serospecific, one may use a polyclonal antiserum against human red blood cells, or a defined mixture of monoclonal antibodies that collectively react with all of the major blood types. The antibody can be coated onto the nucleating particle, or can be slurried or dissolved in a suitable liquid for impregnation into the absorbent pad. There is generally a minimum amount of antibody that must be used in the blood separation device in order to remove substantially all of the red blood cells from the whole blood. However, it is not possible to give a specific amount of an antiserum that must be used since different antisera differ in their ability to bind red blood cells. Accordingly, the optimum amount of antibody is determined empirically, which can be readily effected by one skilled in the art. Serial two-fold dilutions of neat antibody-containing solution or antiserum are applied to filters along with the desired nucleating agents in an amount sufficient to saturate the filter. Efficiency of filtration, lysis of red blood cells, and amount of plasma that passes through the filter when a standard amount of whole blood is applied are measured.

Other types of agglutinating agents for red blood cells include polymeric amino acids such as polylysine, polyarginine, and the like.

Nucleating Particles

The nucleating particles for use in the present invention are particles which are capable of acting as nucleating agents and which do not react with any of the components of the blood to interfere with subsequent assays. These particles have an average diameter of from about 0.1 micron to about 100 microns, and preferably less than about 10 microns in diameter. When the particles are much greater in diameter than 100 microns it is difficult to impregnate the particles into the pad matrix. Ideally, the nucleating particles are the same size or smaller than the red blood cells themselves.

Particles useful in the present invention are those to which lectins or other agglutinating agents can be conjugated so as to lie on the surfaces of the particles. The conjugation may be covalent or noncovalent in character, and may be direct or indirect (i.e., by means of a bispecific linking agent). For example, the porous iron oxide particles used herein are magnetizable polyacrolein beads which contain iron oxide. These beads have reactive aldehyde groups on the surface thereof which link with lectins upon contact. Alternatively, the lectin or other agglutinating agent can be chemically immobilized onto the surface of the nucleating particles. Nonlimiting examples include lectin which has been immobilized onto silica, lectin which has been immobilized onto glass beads, or lectin immobilized onto agarose. These nucleating particles with agglutinants on their surfaces thus allow red blood cells to agglutinate around them on their surfaces to form large clumps, or clusters.

Many other inert particles that permit absorption, adsorption, or immobilization of lectins or other agglutinating agents on their surfaces can also be used as nucleating particles in the present invention. Among these particles are latex beads, glass beads, cellulose, titanium dioxide, polyacrolein, alumina, iron oxide, chromium oxide, and the like.

For purposes of the present invention, the preferred nucleating particles are polyacrolein or polyacrolein/iron oxide beads. However, as shown in Table 2, many types of particles can be used, and the invention is not limited to any specific particles. Additionally, combinations of nucleating particles can be used, in any desired proportions.

TABLE 2

| Reactive agglutination rate enhancement of different nucleating particles | |
|---|---|
| Particle | Relative Agglutination Rate |
| free lectin | 1 |
| free lectin + silica | 1 |
| lectin attached to polyacrolein bead | 2 |
| lectin attached to 0.3 micron latex | 20 |

The present invention requires that some free agglutinating agent be mixed with the nucleating particles. This is unlike conventionally coated particles, which are prepared by mixing the particles with the agglutinating material to be used, maintaining the particles in contact with the agglutinating material for sufficient time to adsorb, absorb, or conjugate the agglutinating material to the particles, and then washing the particles to remove excess agglutinating agent.

Conventionally prepared coated particles are thus substantially free of agglutinating agent that has not been absorbed, adsorbed, or conjugated to the particles.

Formation of the Mixture

The desired mixture is preferably formed by first mixing nucleating particles with an excess of agglutinating agent. As a result, some of the agglutinating agent becomes intimately associated with the particles, and the remainder remains free. This mixture is then incubated with the RBCs.

Alternatively, the particles can be added to the RBCs first, and then agglutinating agent added, or the agglutinating gent added first, and then in the particles. The net result is still that the RBCs are contacted with a mixture of free and nucleating particle-bound agglutinating agent.

Cluster Forming Means

The cluster forming means comprises any suitable material through which plasma or serum can pass, which is inert to whole blood and which does not interfere with subsequent assays of the blood sample, in combination with a mixture of at least one agglutination agent and nucleating particles. While the particles may be coated with or have absorbed, adsorbed, or conjugated thereto agglutinating agent, i.e., the particles must be somehow intimately associated with agglutinating agent, there is preferably some free agglutinating agent present in the cluster forming means. In general, approximately 25–85% of agglutinating agent is in a free state, and the remainder is intimately associated with the particles in the cluster forming means. More preferably from about 30–75% of the agglutinating agent is associated with the particles as free agglutinating agent, while the remainder of the agglutinating agent is intimately associated with the particles.

A particularly useful cluster forming means is a absorbent pad which contains a combination of agglutinating chemicals and nucleating particles.

Agglutinating chemicals and nucleating particles are preferably incorporated into the absorbent pad by impregnation thereof, and the pad is subsequently dried. Optionally, an anticoagulant is used in the absorbent pad, e.g., EDTA or sodium heparinate.

In another embodiment, high molecular weight polyethylene glycol is also incorporated in the pad. Table 1 shows ranges for combinations of agglutinating agents and nucleating particles that can be used in the present invention. In Table 1, the rate of agglutination was rated from 1 to 4, with 4 being the fastest and 1 being the slowest. The concentration of each component is expressed in terms of the impregnating solution. Lectin is present in each experiment.

TABLE 1

| 1a) Effect of lectin concentration (*Phaseolus vulgaris*) on agglutination rate | | | | | |
|---|---|---|---|---|---|
| Lectin conc. (mg/mL) | 0 | 100 | 200 | 300 | 400 |
| Agglutination rate | 1 | 3 | 4 | 4 | 4 |
| 1b) Effect of nucleating particle (polyacrolein/iron oxide) concentration on agglutination rate | | | | | |
| Particle conc. (mg/mL) | 0 | 22 | 44 | 66 | 88 |
| Agglutination rate | 2 | 4 | 4 | 4 | 4 |
| 1c) Effect of molecular weight of PEG on agglutination rate | | | | | |
| MW of 5% W/V PEG | 6000 | 8000 | 10000 | 20000 | 35000 | 40000 |
| Agglutination rate | 1 | 1 | 2 | 4 | 4 | 4 |

The concentrations of agglutinating agent and nucleating agent are chosen so as to form clusters from substantially all of the red blood cells in a sample. Typically, the agglutinating agent will be present in a concentration ranging from about 10 to about 4500 micrograms/mL, and the nucleating particles will be present in a concentration of from about 0.1 to about 20 mg/mL. Where optional polyethylene glycol is used with the agglutinating agent, the polyethylene glycol is used in concentrations of approximately 0.1 to 30% w/v solution.

A buffered solution may be used to impregnate the absorbent pad with the agglutinating agent and nucleating particles and, where used, polyethylene glycol. This buffer may include phosphate buffered saline, tris MOPS, borate, carbonate, or the like. Usually, the solution is buffered to a pH in the range of about 4 to 9. The concentrations of agglutinating agent, nucleating particles, and polyethylene glycol in the buffered solution are about 10 to 400 micrograms/mL, about 0.1 to about 20 mg/mL, and about 0.1 to about 30% w/volume, respectively.

In the case of cholesterol assay, as illustrative of other assays, the impregnating solution has from about 2 to about 100 units/mL of the two enzymes, cholesterol esterase and cholesterol oxidase. The detergents, if used, have a total weight of from about 0.1 to about 5 weight percent of the medium. The binding agents or adhesives are generally in the range of about 0.2 to about 10 ore more, usually rom about 1 to about 5 weight percent of the medium. The binding agents are adhesives are generally in the range of about 0.2 to about 10 or more, usually from about 1 to about 5 weight percent of the total detergent mixture. A preservative or hydrogen bonding agent may be present in from about 1 to about 20 weight percent of the total detergent mixture. A preservative or hydrogen bonding agent may be present in an amount of from about 1 to about 20 weight percent, more usually from about 2 to 10 weight percent. The remaining additives are generally present in a total amount of less than about 10 weight percent. The remaining composition may be water, nonreactive ingredients, excipients, extenders, and the like.

Removal Means

The red blood cell clusters may be removed by any suitable means, including physical means such as filtration, sedimentation, and centrifugation, and chemical means such as by binding to an immobilized agent which preferentially binds the clusters. (The later agent may be, for example, an immobilized sugar which is bound by a lectin agglutinating agent. The immobilized sugar will bind free lectin, particle-bound lectin, and agglutinated clusters of RBCs including lectin molecules with free sugar binding sites). Filtration is preferred.

The preferred filtration means is a porous absorbent pad which, by virtue of its absorbency, can be impregnated with agglutinating agent and nucleating particles so as to serve also as a cluster forming means.

Pads made from materials such as glass or synthetic fibers can be used. The pads can be woven or nonwoven. The fibers are preferably hydrophilic, either by the nature of the fibers themselves or by post-treatment of the fibers. The fiber size is not material.

The clusters formed range in size from about 100 to about 1500 microns. Most clusters fall into the range of from about 250 microns to about 1000 microns.

The mesh or pore size of the pad should average about 200 microns, with a preferred range being from about 20 to about 500 microns.

One particularly suitable material for the absorbent pad is Orlon® fibers in a pad approximately ⅛ inch thick, with an average pore size of about 200 microns.

The Secondary Filter

Optionally, a secondary filter is used to trap any extra red blood cells that may escape from the absorbent pad. This secondary filter may be made of any filtration material which is compatible with the assay and which is capable of separating red blood cells from plasma. For example, it can be made of glass fiber paper, filter paper, or synthetic filter materials such as porex filter. The secondary filter should ideally have a very small pore size to permit plasma to pass while retaining any residual red blood cells. Ideally, a porous matrix with pore sizes between 1 and 5 microns can be used. A glass fiber filter with a mean pore size of 1.2 microns and a thickness of 737 microns is preferred, although a much thinner porous filter can also be used. Conveniently, when a secondary filter is provided, it is configured as the second layer of a two layer device.

Flow Delay Coating

The present invention also optionally provides a coating on a substrate to inhibit flow of a liquid through the substrate for a predetermined period of time. After a predetermined period of time, the liquid is completely released through the substrate. There is substantially no effect on the viscosity and flow characteristics of the fluid. The rate of flow delay, i.e., the length of time the liquid is retained on the substrate, is controlled by the amount of coating applied to the substrate. The control means is self-regulating.

For example, a coating is applied to a pad made of paper, glass fiber, fabric, or similar materials to provide flow-control means for use in diagnostic devices. These pads retain fluid for a discrete period of time to enable substances in the fluid to react with components in the pad for a discrete period of time, after which the fluid flows completely through the pad. Different types of reactions that require different incubation times can all use the same type of pad with differing levels of coating applied to correspond to the desired delay time. The coating materials do not chemically affect the reagent mixture, nor do they affect the viscosity of the sample or reagent fluid, and thus do not affect the flow of the reagent fluid or the run time of a reagent strip portion of an assay device.

For the purpose of the present invention, "flow delay" means that the flow of a fluid through a material is delayed for a certain length of time, after which the fluid flows substantially completely through the pad. For example, for the critical period of time., from introduction of the sample, $t_c$, to $t_c$, the flow rate is such that in this time period no more than 10%, and preferably no more than 5%, of the sample flows through the material. After $t_c$, substantially all of the remainder of the sample passes through the flow delay material. Moreover, the rate of flow after $t_c$ should be substantially greater than the rate of flow before $t_c$, as the sizing material does not increase the viscosity of the sample.

As different reactions require different incubation times, $t_c$, preferably ranges from 2 seconds to twenty minutes. $t_c$ more preferably ranges from 2.5 seconds to about 5 minutes. Particularly for quantative assays, the amount of sample retained in the flow delay material must be a sufficient amount of sample to be incubated in the flow delay material to effect a valid assay. Likewise, the amount of sample which passes through the flow delay material must be a sufficient amount of sample to effect a valid assay.

The flow delay means of the present invention, in other words, acts like a timed valve, in that the fluid is retained in the flow delay means for a predetermined time, $t_c$. After this time $t_c$, the fluid flows substantially completely through the flow delay means, such as into an adjoining layer of an assay device.

Once the flow delay means has "opened" to the fluid, at $t_c$, it is important that substantially all of the fluid flow through the flow delay means rather than remain in the flow delay means. The flow delay means retains the fluid in the flow delay area only for a predetermined time, and then permits the fluid to flow through the flow delay means substantially without changing the fluid. The flow delay means does not affect the viscosity of the fluid, nor does the flow delay means add extraneous material to the fluid sample from the flow delay means. The fluid is free to flow directly through the flow delay means just as if a mechanical valve had been opened, and substantially all of the fluid flows through this "valve" without being retained in the flow delay means.

One way of expressing the fluid flow through the flow delay means is in terms of the time required for the sample to pass completely through the flow delay means once the predetermined time, $t_c$, has passed. This time period from initial contact of the fluid sample with the flow delay means, $t_c$, to the predetermined time, as noted above, can be expressed as $t_c$. The time required for the sample to flow through the flow delay means after $t_c$ can be expressed as $t_f$. Ideally, $t_f$ should not be much greater than $t_c$, and may often be smaller than $t_c$, depending upon the length of time the sample is retained by the flow delay device, the nature of the sample, and subsequent operations to be performed on the sample.

For example, if $t_c$ is one minute, $t_f$ can be from less than one minute to greater than five minutes, depending upon the initial viscosity of the sample, the rapidity with which the test must be conducted, and the like. On the other hand, if $t_c$ is 20 minutes, it may be useful for $t_f$ to be less than 20 minutes. Depending upon the type of sample applied to the flow delay means and the rate at which one desires the sample to flow through the device, one can adjust $t_c$ and $t_f$ so that they are multiples of each other. One skilled in the art can readily determine the relationship between $t_c$ and $t_f$ which is optimum for the particular fluid sample to be treated, and can adjust the flow delay means accordingly.

In another example, with a relatively viscous fluid sample which only requires an incubation of one minute, $t_c$ can be one minute and $t_f$ can be up to about ten minutes. On the other hand, for a relatively free-flowing sample which requires a long incubation period, such as 20 minutes, $t_f$ can be a fraction of $t_c$, i.e., 5 minutes, or ¼ $t_c$. The relationship between $t_c$ and $t_f$ is not critical to the invention; the criticality is that the flow delay means act as a means to retain the fluid sample for a predetermined time, and then release the sample through the flow delay means.

A great many materials can be used to control the flow of liquids through substrates, depending upon the type of fluids used. Examples of these materials include alkyl ketene dimers, alkenyl succinic anhydrides, and fluorocarbon resins, either alone or with other materials such as saccharides, low molecular weight polymers, waxes and the like. Since not all materials offer equivalent degrees of fluid retention, the material used to coat or impregnate the substrate can be chosen to provide the desired flow delay time for the fluid to be controlled. These coating materials for flow delay are designated "sizing materials" for the purpose of the present invention.

A number of sizing materials can be applied to fibrous substrates, such as pads, which retain fluids in the substrate for a predetermined discrete period of time. This time period can range from less than one minute to more than 20 minutes, depending upon the fluid, the nature of the sizing material, and the amount of sizing material applied to the substrate.

The flow control means of the present invention has the following features and advantages:

The degree of flow control means is readily metered by the amount of sizing material applied to the substrate.

The sized substrates are self-regulating, and require no designed-in moving parts and no input from the user for accurate operation.

Different types of reactions that require different incubation times can all use the same type of pad with differing levels of sizing material applied corresponding to the desired flow delay.

The delay times obtained are highly reproducible.

The sizing materials used for flow delay are inexpensive and are easily and accurately dispensed onto the substrate material.

The sizing material do not chemically affect reagents used in clinical assays.

The sizing materials used do not affect the viscosity of the reagent fluid or the sample and thus do not affect the flow of the reagent fluid or the run time of the reagent strip portion of the device.

Some of the sizing material can be covalently attached to the substrate, particularly if the substrate is paper or a surface-modified glass fiber material.

By putting a flow delay coating on the secondary filter pad, the sample can be retained in the primary filter pad for an extra 5–10 seconds, so that the whole blood sample can be incubated with lectins and other chemicals. While the whole blood is maintained in the primary filter pad for the extra incubation period, most of the large particles formed are trapped in the ABS pad, and few or no red blood cells enter the bottom of the secondary filter pad. This time delay mechanism worked very well, and a delay of as little as 5–10 seconds actually helped to reduce the total flow time through the device by more than 25%. In addition, no red blood cell leakage was observed.

Reagent Means

The red blood cell separating means can be used with any assay device which includes a reactant pad through which fluid flows to produce a detectable signal. After addition of the sample to the reactant pad through the red blood cell separation means, and an incubation of up to about 30 minutes, the analyte reacts with the reagents in the reactant pad to produce a detectable signal.

The red blood cell separation device can, of course, be used with assay devices for a great variety of substances in the blood in addition to cholesterol, including glucose, blood urea nitrogen, uric acid, albumin, creatinine, bilirubin, phosphate, total protein, amylase, calcium, etc.

The red blood cell removing means of this invention can be used with any type of assay that can be conducted using a reactant or reagent zone for reaction with the analyte of interest. A variety of sophisticated reagents, protocols or regimens can be devised based upon a limited amount of material migrating to produce a boundary in proportion to the amount of material present. Examples of protocols include particles having first and second ligands, where the first ligand competes with analyte for receptor bound to a surface. After carrying out competition for a limited amount of receptor between analyte and sample pad and the particle transported with the effluent through the measurement region. By having receptor for the second ligand in the measurement region, the particle boundary will be defined by the number of particles added to the pad. By having colored particles, charcoal particles, magnetic particles, dyes, dye- polymer conjugates, protein with high visible extinction coefficients, etc., the boundary will be readily defined.

Any technique which allows for binding of a detectable entity in proportion to an analyte of interest may be employed. These may include cleavage of a bond to release the entity, where the bond to the entity is not cleavable when the entity is bound to a receptor, binding to a support which inhibits migration of the entity in proportion to the amount of analyte in a sample, or the like. The entity may be a particle as described above, an enzyme which catalyzes the production of a detectable product, or the like.

Of particular interest is where a product is produced on the sample pad which provides for a detectable boundary. For example, where the analyte is an enzyme substrate, the sample pad may be impregnated with the appropriate enzyme or enzymes to produce a product. Normally, the enzyme product will react, either directly or indirectly, with a compound which is fixed in the assay measurement region. This may be exemplified by cholesterol, glucose, or the like, which reacts with an oxidase to provide an oxidizing species. The oxidizing species may then react with the bound compound to produce a detectable boundary. Illustrative of this situation would be the hydrolysis of serum cholesterol ester by cholesterol esterase and subsequent oxidation of cholesterol by cholesterol oxidase to produce a stoichiometrically identical amount of hydrogen peroxide. This hydrogen peroxide is formed at a stationary reaction pad and combines with horseradish peroxidase which is in the mobile phase. The horseradish peroxidase/hydrogen peroxide reacts with a bound substrate to produce a detectable boundary.

Depending upon the assay, other reagents may also be present. For example, detergents can be used where a lipophilic analyte in blood is involved, where the lipophilic analyte binds to proteins bound to blood. This may be illustrated by cholesterol which binds to proteins, as for example, in very low, low and high density lipoproteins. Thus, detergents such as nonionic, anionic or cationic detergents may be used. Of particular interest are polyoxyalkylene, ethoxylated alkylphenol, octylphenoxypolyethoxyethanol, octylphenol-ethylene oxide condensates and polyoxyethylene lauryl ether, or anionic detergents, such as bile acids, e.g., sodium cholate and sodium taurocholate. In addition, various sticking agents or adhesives which are substantially noninterfering, which may include gelatin, casein, serum albumin, or gamma globulins may be incorporated in the reagent pad. Also, the reagent pad may include preservatives, such as sucrose, polyvinyl alcohol, polyvinyl pyrrolidone, dextran,as well as catalase inhibitors such as sodium azide or hydroxylamine salts.

The Apparatus and Method

Red blood cells are rapidly removed from a sample of whole blood using the blood separation device 10 of the present invention as shown in FIG. 1. Whole blood is introduced to the absorbent pad 1, which absorbent pad is impregnated with a mixture of an agglutinating agent and nucleating particles. Most of the separation of red blood cells occurs in the absorbent pad, where the red blood cells are agglutinated into large clusters which are retained in the absorbent pad. The blood then rapidly passes into the secondary filter 2 for final separation of any left over red blood cells that may remain in the sample. Since white blood cells, which only occupy about 1% of the total volume of blood, are much larger than red blood cells, the white blood cells are trapped by the filter.

FIG. 1 illustrates one embodiment of the invention. When whole blood is introduced into the absorbent pad 1, the red blood cells contact the mixture of agglutinating agent and nucleating particles and agglutinate very quickly, e.g., in less than 5 seconds, into large clumps of cells. The clumps have an average diameter of about 500–1000 microns. The red blood cell aggregates remain in the absorbent pad because the pore size of the pad is small enough to retain the aggregates.

The plasma, which is now predominantly red blood cell free plasma, flows into the secondary filter 2. The secondary filter 2 traps any extra red blood cells that escape from the absorbent pad.

Figure 2:
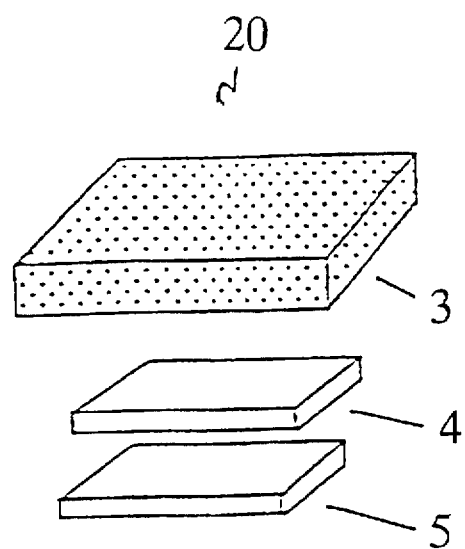
FIG. 2 shows a device according to the invention with an optional secondary filter.

FIG. 2 shows an optional third layer 3 which has an agglutinating agent deposited thereon. This third layer is present to ensure a plasma substantially free of red blood cells for particularly sensitive assays.

Figure 3:
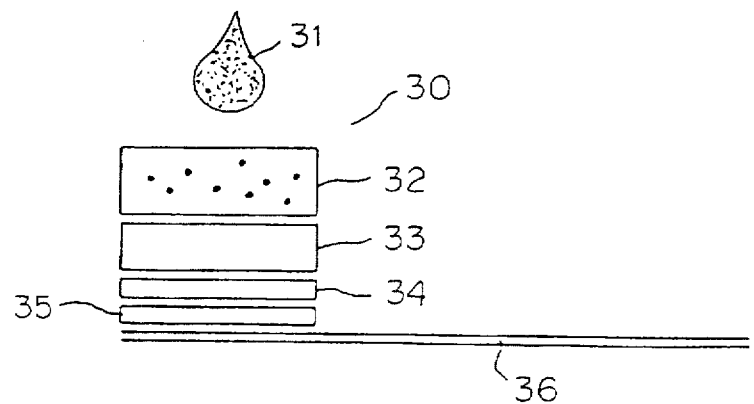
FIG. 3 shows the device according to the invention incorporated in a diagnostic device.

FIG. 3 shows an assay device 30 incorporating the blood separation means of the present invention. Whole blood 31 is introduced to the device through the absorbent pad 32. This absorbent pad is impregnated with a mixture of a lectin and beads of acrolein/iron oxide which have been coated with a lectin. Most of the red blood cells in the sample agglutinate almost immediately upon contact with the absorbent pad, and are retained in this part of the device. Blood which is substantially free of red blood cells flows to the secondary separation pad 33. This pad is made of 1.2 micron glass fibers, and traps any red blood cells that were not agglutinated and retained in the absorbent pad. The sample then flows to the enzyme pad 34 that contains the cholesterol enzymes (cholesterol esterase and cholesterol oxidase). After cholesterol in the sample is converted to hydrogen peroxide, the sample passes through pad 35, the time delay pad, and finally contacts the measurement dye zone 36. The measurement dye zone 36 is coated or impregnated with an indicator material that reacts with the enzyme-treated sample to give an indication of the presence or amount of analyte in the sample.

Figure 4:
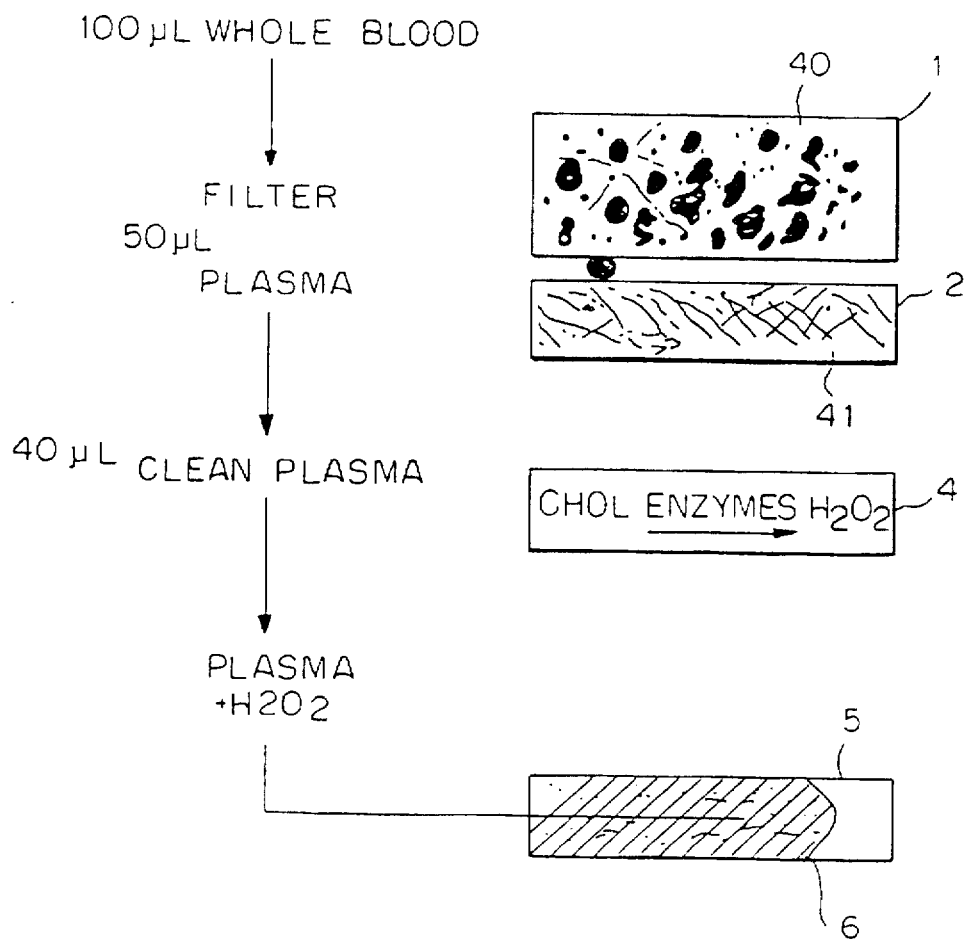
FIG. 4 is a schematic showing the operation of the device of FIG. 3.

FIG. 4 illustrates the used of the device according to the present invention for a cholesterol determination. Of course, the device can be used with a great variety of clinical assays, and this illustration is not intended to limit the invention to one type of assay.

Referring to FIG. 4, a sample of whole blood, generally approximately 100 microliters, is introduced into an absorbent pad 1. The red blood cells present in the whole blood agglutinate into large (500–1000 micron) clusters 40 around nucleating particles and are trapped in the absorbent pad. Any small clumps 41 that leak through the absorbent pad 1 with the plasma are trapped by the secondary glass fiber pad 2. Plasma then enters the enzyme pad 4. The enzyme pad is impregnated with cholesterol esterase and cholesterol oxidase. The cholesterol in the plasma reacts with these enzymes to produce hydrogen peroxide.

The hydrogen peroxide in the plasma then flows into the measurement zone 5 that contains a dye immobilized thereon. This dye reacts with horseradish peroxidase to form a color bar 6, the length of which is related to the amount of cholesterol in the sample.

The following examples illustrate the capacity of the device of the present invention to remove red blood cells from whole blood. These examples are included for purposes of illustration and comparison only, and are not intended to limit the scope of the invention.

EXAMPLE 1

The device shown in FIG. 1 (10) has an absorbent pad 1 made of Orlon® fibers from Lydal Westrex with dimensions of 9.0 mm×6.1 mm×2.1 mm. A solution of 125 U/mL lectin in 5 mM phosphate buffered saline, pH 7.2, was made up. Seventy microliters of this solution was mixed with 1.4 mg of polyacrolein/iron oxide particles of size about 1–20 microns, with a mean particle size of about 10 microns. This mixture, which comprised polyacrolein/iron oxide particles coated with a mixture of lectin and free lectin in solution, was added to the pad, which absorbed the liquid. The pad was air dried for twelve hours at 70° F. and 5% relative humidity.

A secondary filter (2) was made from a glass fiber Whatman GD1 filter material cut to dimensions of 7.2 mm×5.5 mm×1.4 mm. This secondary filter was placed below the absorbent pad.

The device as prepared above was tested by depositing 140 microliters of whole blood having a hematocrit of 40–50% red blood cells onto the absorbent pad. The effectiveness of separation of red blood cells from whole blood was tried with a variety of agglutinating agents and nucleating agents. The speed of separation, the amount of plasma recovered, and the amount of red blood cell leakage, are shown in Table 3. A rating of 0 RBC leakage represents no blood cell leakage, and the plasma sample is visibly clear. A rating of 4 represents that the plasma recovered contained more than 20% red blood cells.

TABLE 3

|  | YIELD OF PLASMA (uL) | SEPARATION TIME (sec.) | RBC LEAKAGE |
|---|---|---|---|
| 1. ABS. PAD + GD1 | 15 | 192 | 4 |
| 2. FREE LECTIN (GD1) | 25 | 25 | 0.5 |
| 3. LECTIN + BEAD (GD1) | 32 | 5 | 0 |
| 4. LECTIN ON SILICA (GD1) | 34 | 42 | 1 |

The free lectin concentration on the blood separation pads (the absorbent pad 1 as shown in FIG. 1) was evaluated with HPLC. The pads were evaluated after they were manufactured. Free lectin was extracted from pads that had passed a functional test to determine if sufficient reagents were present in the pad to run a reliable assay, and the working range of free lectin concentration in the pads was established. The percentage of free lectin vs. bound lectin in the formulation was confirmed using the HPLC method.

An HPLC system was used to resolved isolectins from phaseolis vulgaris on a TSK SK CM. The column was a carboxy methyl cation exchanger with a polymer gel base, coupling both gel filtration with cation exchange as a means of separation of proteins. Because of the large void volume of the column, the minimal level of quantitation was 10.0 mg/mL.

A CM silica based column was then used, this column having a substantially smaller column volume. This smaller column performed as well as the polymer based TSK column with a 2-order reduction in sample load. The parameters for resolving isolectin by the CM300 column were as follows:

1. Equipment:
   Waters 625 Pump
   Waters 171 Autosampler
   Waters 996 Photodiodearray detector
2. Conditions:
   Column: Syn Chrom CM300
   Dimensions: 100 mm/4.6 mm ID/10 micron
   Mobile Phase: B: 100% $dH_2O$, 0.01M citric acid pH=4.4 D: 100% $dH_2O$, 0.01M citric acid pH=4.4, 0.5M NaCl
   Flow Rate: 0.7 mL/minute
   Run Time: 45 minutes
   Detection: 200–350 nm
   Wavelength 276 nm
   Sensitivity: 0.01 AUFS
   Column Temperature Ambient
   Injection volume: 100 microliters
   Sample [C] 0.5 mg/mL
   W600 Gradient Table

| # | Time (min) | Flow (mL) | % A % | % B % | % C % | % D % | Curve |
|---|---|---|---|---|---|---|---|
| 1 | 0.00 | 0.70 | 0.0 | 100.0 | 0.0 | 0.0 | 0 |
| 2 | 5.00 | 0.70 | 0.0 | 100.0 | 0.0 | 0.0 | 1 |
| 3 | 20.00 | 0.70 | 0.0 | 0.0 | 100.0 | 0.0 | 6 |
| 4 | 40.00 | 0.70 | 0.0 | 0.0 | 0.0 | 100.0 | 11 |
| 5 | 45.00 | 0.70 | 0.0 | 100.0 | 0.0 | 0.0 | 6 |

It was thus determined that about 54.5% free agglutinating agent, plus or minus 30%, was the optimum amount of free agglutinating agent which provides superior separation of red blood cells when used in conjunction with nucleating particles which are intimately associated (coated, etc.) with an agglutinating agent. From this, about 45.5% of the lectin, plus or minus 30%, was formed to be intimately associated with the particles (i.e., was not washed off the particles by the above-described process).

EXAMPLE 1

A separation device 20 as shown in FIG. 2 was prepared having an absorbent pad 1 made from Orlon® fibers from Lydall Westex with dimensions of 9.0 mm×6.1 mm×2.1 mm. A solution of 125 U/L lectin in 5 mM phosphate buffered saline, pH 7.2, was made up. Seventy microliters of this solution was mixed with 1.4 mg of acrolein/iron oxide particles to form a mixture of coated particles and free lectin; the mixture was added to the pad, which absorbed the liquid. The pad was air dried for twelve hours at 70° F. and 5% relative humidity.

A secondary filter (2) was made from whatman GD1 filter material cut to dimensions of 7.76 mm×5.5 mm×0.5 mm. This secondary filter was placed below the absorbent pad.

A third filter (4) was placed below the secondary filter. This third filter also had dimensions of 7.7 mm×5.5 mm×0.5 mm.

The absorbent pad in each trial was made of S&S grade 404 filter paper. Each absorbent pad was impregnated with 3 micrograms of free lectin 0.5 mM PBS, pH 7.2, and air dried prior to assembling the device.

The devices were tested by depositing 140 microliters of whole blood having a hematocrit of 40–50% red blood cells onto the absorbent pad. Leakage of red blood cells is shown in Table 4, demonstrating that absorbent pads made of fibers other than glass were as effective as corresponding absorbent pads made of glass fibers.

TABLE 4

|  | Yield of Plasma | Separation Time (sec.) | RBC Leakage |
|---|---|---|---|
| ABS. PAD + S&S40 + S&S5-S | 40 | 20 | 0 |
| ABS. PAD + S&S40 + S&S404 | 29 | 19 | 0 |
| ABS. PAD + S&S5-S + S&S404 | 26 | 20 | 0 |

EXAMPLE 3

In this example, lectins purified from Phaseolus vulgaris were used as in Example 1 to impregnate the absorbent pad. Lectins purified from Phaseolus vulgaris were found to be the most effective and the most non-specific for different blood types. However, mixtures of two or more types of lectins have also been found useful in separating red blood cells. In all cases, free (unbound) lectins in combination with nucleating particles decreased the separation times by 3- to 5- fold when compared with the results with free lectins alone. The absorbent pads and the mixture of lectin and nucleating particles used were the same as in Example 2.

TABLE 5

|  |  | Yield of Plasma (μL) | Separation Time (sec.) | RBC Leakage |
| --- | --- | --- | --- | --- |
| LECTIN | TYPE O | 25 | 25 | 0.5 |
| LECTIN + BEAD | TYPE O | 32 | 5 | 0 |
| LECTIN | TYPE A | 30 | 34 | 0 |
| LECTIN + BEAD | TYPE A | 39 | 7 | 0 |
| LECTIN | TYPE AB | 26 | 25 | 0 |
| LECTIN + BEAD | TYPE AB | 34 | 6 | 0 |

EXAMPLE 4

Experiments were conducted to demonstrate that free agglutinating agent alone is not at effective as a mixture of nucleating particles and free agglutinating agent, and that nucleating particles which are coated with agglutinating agent without the presence of free agglutinating agent, are not as effective as is the combination of nucleating particles in the presence of free agglutinating agent in separating red blood cells from a sample.

A device was prepared as shown in FIG. 1. The device had an absorbent pad made of Orlon® fibers from Lydall Westex. The pad had dimensions of 9.0 mm×6.1 mm×2.1 mm. A solution of 125 U/mL lectin in 5 mM phosphate buffered saline, pH 7.2, was made up. Seventy microliters of this solution was mixed with 1.4 mg of polyacrolein/iron oxide particles of size about 1–20 microns, with a mean particle size of 10 microns. The mixture was added to the pad, which absorbed the liquid. The pad was air dried for twelve hours at 70° F. and 5% relative humidity.

A secondary filter was made from a glass fiber Whatman GD1 filter material cut to dimensions of 7./2 mm×5.5 mm×1.4 mm. This secondary filter was placed below the absorbent pad.

The device as prepared above was tested by depositing thereon 140 microliters of whole blood having a hematocrit of 40–50% red blood cells onto the absorbent pad. The effectiveness of separation of red blood cells from whole blood was tried with a variety of combinations of agglutinating agents and nucleating agents. The speed of separation, the amount of plasma recovered, and the amount of red blood cell leakage were measured. A rating of 0 RBC leakage represents no blood cell leakage, and the plasma sample is relatively clear. A rating of 4 represents that the plasma contained more than 20% red blood cells. The results are shown in Table 6.

TABLE 6

|  | Yield of Plasma (μL) | Separation Time (sec) | RBC Leak |
| --- | --- | --- | --- |
| ABS. PAND + GD1 | 192 | 4 | 15 |
| FREE LECTIN (GD1) | 25 | 25 | 0.5 |
| LECTIN + BEAD | 32 | 5 | 0 |
| LECTIN ON SILICA (GD1) | 34 | 42 | 1 |

In Table 6, lectin+bead refers to polyacrolein/iron oxide beads containing 29.5% free lectin and 72.5% bound lectin. The amount of free agglutinating agent present was determined by centrifuging the beads in the reagent down, and assaying the amount of free lectin by conventional protein assay.

In Table 6, lectin on silica refers to silica beads onto which lectin is chemically bound (immobilized). The silica beads onto which lectin is chemically bound are substantially free of free lectin.

It is clear from Table 6 that adding free lectin alone to plasma improved the yield of plasma while shortening separation time. Likewise, silica particles onto which lectin was immobilized, in the substantial absence of free lectin, also improved the yield of plasma while shortening separation time. The silica particles onto which lectin was immobilized were not as effective in removing red blood cells from plasma, nor as rapid as free lectin alone. The combination of free lectin in combination with nucleating particles was found to be the most effective in giving clean, efficient and fast plasma separation.

EXAMPLE 5

Further testing was conducted to demonstrate that the most effective means for separating red blood cells is with a mixture of agglutinating agent and nucleating particles (coated with agglutinating agent), rather than with free agglutinating agent alone or with nucleating particles coated with agglutinating agent and with no free agglutinating agent in the mixture.

Particles were prepared which were coated with lectin and in which there was no free lectin mixed with the particles. These particles (and fibers) were prepared by conventional lectin-coating methods, i.e., the particles or fibers were mixed with lectin, filtered, and washed with conventional wash solution to remove free lectin from the particles. The free lectin was assayed by centrifuging the beads in the reagent down and assaying the amount of free lectin by conventional protein assay. It was found that substantially no free lectin was mixed with these particles.

Samples were treated with these particles as described in Example 4, and the separation times and red blood cell leakage are shown in Table 7.

TABLE 7

|  | Separation Time | Red Blood Cell Leakage |
| --- | --- | --- |
| Agarose beads | >40 sec | 4 |
| Cellulose particles | >40 sec | 4 |
| Silica particles | >40 sec | 2 |
| Orlon fibers | >40 sec | 4 |

Comparing the separation times and red blood cell leakage for particles coated with agglutinating agent wherein there is free agglutinating agent present, with beads coated with agglutinating agent in the absence of free agglutinating agent, it can readily be seen that the combination of nucleating particles with free lectin is unexpectedly superior in separating red blood cells quickly and efficiently.

It is clear from the results shown in Table 7 that particles which are merely coated with lectin are inferior in separating red blood cells from a sample as compared with these same particles with are coated with an agglutinating agent but which still have free agglutinating agent (i.e., agglutinating agent in excess of that which is adsorbed, absorbed, or conjugated to the particles).

EXAMPLE 6

Preparation of the flow delay coating

One gram of palmitoyl ketene dimer was dissolved in 25 mL ethyl acetate. This stock solution was diluted to appropriate levels, i.e., to a level that permits mechanical dispensing of the solution into pads in a precise manner. Six micrometer aliquots of a chosen dilution were applied to pre-cut secondary filter pads. The pads were dried in a 100°

C. oven for 30 minutes and cooled in a desiccated atmosphere. The pads were installed in the device of Example 2 as a secondary filter.

EXAMPLE 7
Effect of flow delay on red blood cell leakage

| Amt. of flow delay coating per pad | Approx. flow delay time | Red blood cell leakage |
|---|---|---|
| 0 µg | 0 sec | slight |
| 4 | <5 | very slight |
| 5 | 5–10 | none |
| 6 | >10 | none |

EXAMPLE 8
Effect of Flow Delay Pad on Flow Rate

| Geometry | Ave. Time through pads | Ave. Total flow time |
|---|---|---|
| no flow delay | 34 sec. | 18.6 min. |
| with flow delay | 42 sec. | 14.2 min. |

When the flow delay pads of 5 µg/pad were tested against pads without flow delay the average flow time through the front end pads in the devices was delayed by less than 10 seconds, but the total flow time through the device actually decreased by 4 minutes. Thus, using the flow delay means in the present invention provided a more efficient separation of red blood cells.

The foregoing description of the specific embodiments will so fully reveal the general nature of the invention that others can, by applying current knowledge, readily modify and/or adapt for various applications such specific embodiments without departing from the generic concept, and therefore, such adaptations and modifications should and are intended to be comprehended within the meaning and the range of equivalents of the disclosed embodiments. It is to be understood that the phraseology and terminology employed herein is for the purpose of description and not of limitation.

All patents, patent applications and other literature cited herein are hereby incorporated by reference in their entirety.

What is claimed is:

1. Apparatus for separation of red blood cells from whole blood comprising
   a cluster forming means comprising the combination of a primary filter through which plasma or serum can pass, and a mixture of a free agglutinating agent and a particle-associated agglutinating agent intimately associated with nucleating particles.

2. Apparatus according to claim 1 wherein said free or particle-associated agglutinating agent comprises at least one lectin.

3. Apparatus according to claim 1 wherein at least 25% of said free or particle-associated agglutinating agent is particle-associated agglutinating agent and the remainder is free agglutinating agent.

4. Apparatus according to claim 1 wherein said primary filter is an absorbent pad and the cluster forming means is formed by incorporating said mixture into said pad.

5. Apparatus according to claim 1, wherein approximately 25% to 85% of said free or particle-associated agglutinating agent is free agglutinating agent and the remainder is particle-associated agglutinating agent.

6. Apparatus according to claim 1, wherein approximately 30% to 75% of said free or particle-associated agglutinating agent is free agglutinating agent and the remainder is particle-associated agglutinating agent.

7. Apparatus according to claim 1, wherein said cluster forming means further comprises polyethylene glycol having a molecular weight of about 10,000.

8. Apparatus according to claim 1 further comprising a secondary filter.

9. Apparatus according to claim 8 wherein said secondary filter contains a secondary agglutinating agent, wherein said secondary agglutinating agent is the same as or different from said free or particle-associated agglutinating agent.

10. Apparatus according to claim 8 wherein said secondary filter includes flow-delay means.

11. Apparatus according to claim 10 wherein said flow delay means comprises a coating of a flow-delay substance selected from the group consisting of alkyl ketene dimers, alkenyl succinic anhydrides, fluorocarbon resins, and mixtures thereof.

12. Apparatus according to claim 11 wherein said flow-delay substance further comprises at least one substance selected from the group consisting of saccharides and low molecular weight polymers.

13. Apparatus according to claim 11 wherein said nucleating particles are selected from the group consisting of particles made of polyacrolein, polyacrolein/iron oxide, latex, silica, glass, agarose, and mixtures thereof.

14. Apparatus according to claim 13 wherein said nucleating particles are particles of polyacrolein/iron oxide.

15. Apparatus according to claim 13 wherein said nucleating particles are particles of latex.

16. Apparatus according to claim 13 wherein said nucleating particles are glass particles.

* * * * *